(12) United States Patent
Greller et al.

(10) Patent No.: US 8,342,737 B2
(45) Date of Patent: Jan. 1, 2013

(54) VIBRATIONAL MIXER

(75) Inventors: Gerhard Greller, Goettingen (DE);
Oscar-Werner Reif, Hannover (DE)

(73) Assignee: Sartorius Stedim Biotech GmbH (DE)

( * ) Notice: Subject to any disclaimer, the term of this patent is extended or adjusted under 35 U.S.C. 154(b) by 877 days.

(21) Appl. No.: 12/226,297

(22) PCT Filed: Apr. 24, 2007

(86) PCT No.: PCT/EP2007/003564
§ 371 (c)(1),
(2), (4) Date: Oct. 10, 2008

(87) PCT Pub. No.: WO2007/131594
PCT Pub. Date: Nov. 22, 2007

(65) Prior Publication Data
US 2009/0275121 A1     Nov. 5, 2009

(30) Foreign Application Priority Data
May 11, 2006 (DE) .................... 10 2006 022 306

(51) Int. Cl.
*B01F 11/00* (2006.01)
*B01F 3/04* (2006.01)
(52) U.S. Cl. ............... 366/169.1; 366/102; 366/167.1; 366/256; 366/333
(58) Field of Classification Search ............ 366/102, 366/118, 332, 333, 334, 167.1, 169.1, 255, 366/256
See application file for complete search history.

(56) References Cited

U.S. PATENT DOCUMENTS

| | | | |
|---|---|---|---|
| 1,175,366 A * | 3/1916 | Lucas | 96/332 |
| 2,498,393 A * | 2/1950 | Clewell | 366/274 |
| 2,592,904 A * | 4/1952 | Jackson | 366/168.2 |
| 2,615,692 A * | 10/1952 | Muller | 366/273 |
| 2,681,798 A * | 6/1954 | Muller | 366/118 |
| 4,511,254 A * | 4/1985 | North et al. | 366/118 |
| 4,585,673 A * | 4/1986 | Sigai | 427/213 |
| 4,676,654 A * | 6/1987 | Fleckner | 366/98 |
| 4,737,036 A * | 4/1988 | Offermann | 366/130 |
| 4,979,830 A * | 12/1990 | Munn et al. | 366/102 |
| 4,999,219 A * | 3/1991 | Klinedinst et al. | 427/69 |
| 5,941,635 A * | 8/1999 | Stewart | 366/165.5 |
| 5,985,175 A * | 11/1999 | Fan et al. | 252/301.4 R |
| 6,322,240 B1 * | 11/2001 | Omasa | 366/118 |
| 6,494,613 B2 * | 12/2002 | Terentiev | 366/279 |
| 7,275,856 B2 * | 10/2007 | Koetas et al. | 366/102 |
| 7,537,376 B2 * | 5/2009 | Von Alfthan | 366/142 |
| 2005/0249033 A1 * | 11/2005 | Krause | 366/332 |
| 2008/0117711 A1 * | 5/2008 | Omasa | 366/118 |

FOREIGN PATENT DOCUMENTS

| | | |
|---|---|---|
| CA | 1 224 405 | 7/1987 |
| CH | 283308 A | 9/1952 |
| CH | 560 066 A5 | 3/1975 |
| DE | 1 031 283 A5 | 6/1958 |

(Continued)

*Primary Examiner* — Yogendra Gupta
*Assistant Examiner* — Emmanuel S Luk
(74) *Attorney, Agent, or Firm* — Gerald E. Hespos; Michael J. Porco

(57) ABSTRACT

A vibrational mixer (1), in particular a single-path mixer for use in single-path bioreactors (4) with flexible walls, consisting of a mixer shaft (2) that can be set into longitudinal motions by a drive (8), with at least one mixing element (3), wherein at least one channel (13) is arranged in the mixer shaft with an opening to an interior reactor space (6).

16 Claims, 2 Drawing Sheets

FOREIGN PATENT DOCUMENTS

Figure 1:
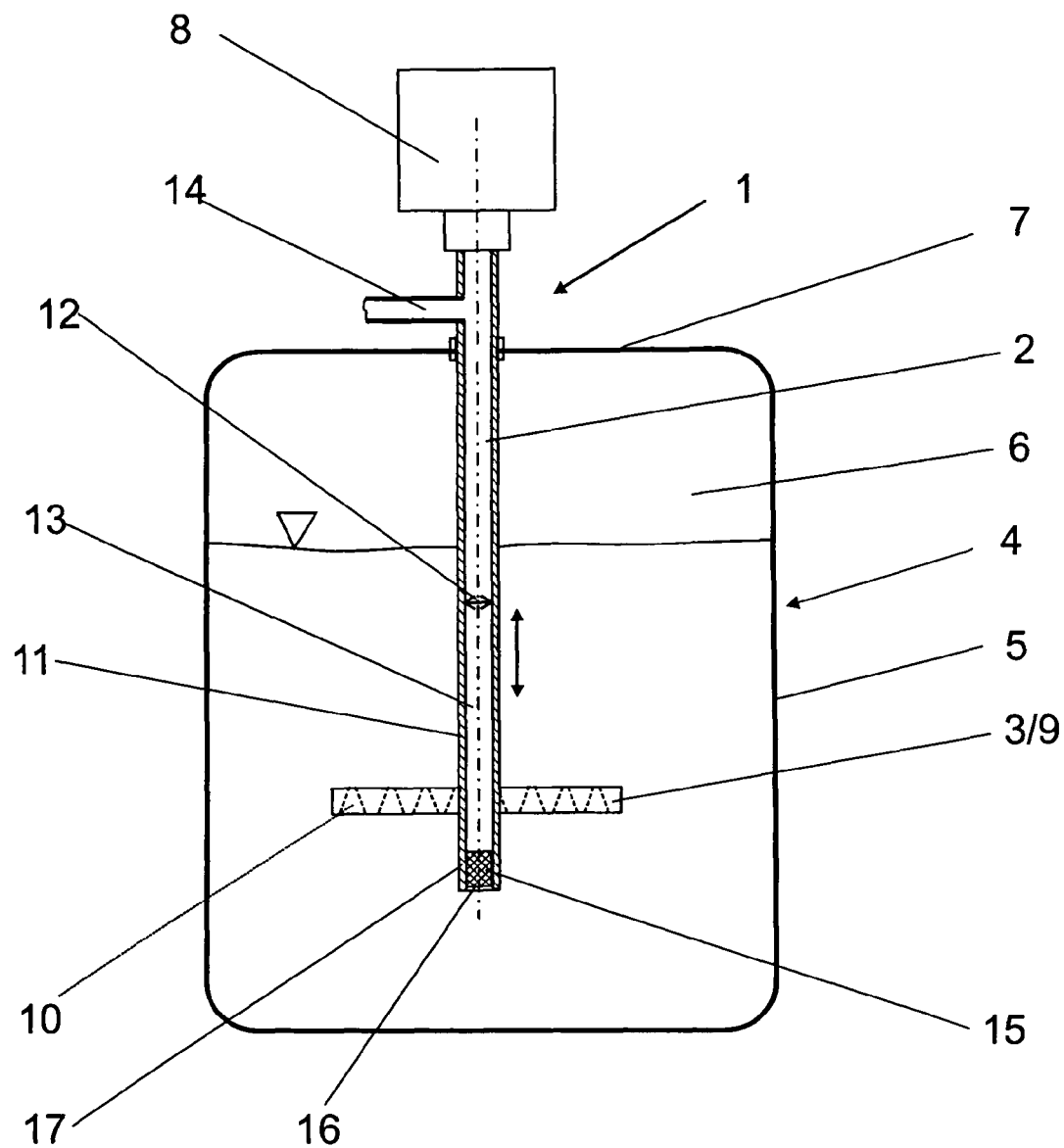

| | | |
|---|---|---|
| DE | 3325969 C2 | 6/1990 |
| DE | 10 2004 003 033 A1 | 8/2005 |
| DE | 10 2004 004 180 A1 | 8/2005 |
| DE | 10 2004 013 078 A1 | 10/2005 |

* cited by examiner

VIBRATIONAL MIXER

The invention relates to a vibration mixer, in particular disposable mixer for use in disposable bioreactors having a flexible wall, the vibration mixer comprising a mixer stem which can be thrown into longitudinal movements by a drive and has at least one mixing element.

Both for reusable bioreactors, generally rigid containers, and also for disposable bioreactors, generally flexible bags or containers having flexible walls, use is made of vibration mixers in order to mix and to cultivate organisms. Vibration mixers have a plate-like mixing element with conical holes (Venturi nozzles). The mixing element in this case is arranged on a mixer stem which is thrown into longitudinal vibrations by a drive.

An example of a vibration mixer is known from US 2005/0249033 A1. Said disposable mixer is arranged in a disposable bioreactor, a bag.

A disadvantage of the known mixer is that further inlets to the reactor interior are required in order to supply gaseous media and liquid media. In particular, the inlets through the container wall are a problem in bioreactors of this type.

A flexible disposable bioreactor which has a vibration mixer is also known from DE 10 2004 013 078 A1. A mixing element which is designed as a mixing plate is also arranged here in the reactor interior at one end of a mixer stem which is guided through the container wall and, outside the container interior, is thrown into longitudinal movements by a drive of a vibration mixer.

Said mixer also has the above-mentioned disadvantages.

It is therefore the object of the present invention to reduce and/or improve the inlets to a bioreactor.

This object is achieved in conjunction with a vibration mixer, in particular, a disposable mixer for use in a disposable bioreactor having a flexible wall [the precharacterizing clause of claim 1] in that at least one duct having an outlet toward a reactor interior is arranged in the mixer stem.

By arranging a duct which opens into the reactor interior in the mixer stem, a separate inlet into the reactor interior is avoided. Since the stem in any case has to be passed through the wall of the bioreactor and therefore at the same time so does the duct arranged in the stem, no further inlet is required. This considerably reduces the manufacturing and the risk of leakages in the container wall.

According to a preferred embodiment of the invention, gas is supplied via the at least one duct, with a gas-injection unit being mounted upstream of the outlet of the duct.

However, the gas-injection unit may also form the outlet itself.

According to a further preferred embodiment of the invention, the outlet is arranged at the free end of the mixer stem, which end faces away from the drive. Gas can therefore be supplied to the reactor interior via the free end of the mixer stem.

According to a further preferred embodiment of the invention, the gas-injection unit is mounted upstream of the mixing element toward the drive. However, it also possible to arrange the gas-injection unit on the mixer stem between two mixing elements. In this case, gas can be supplied to the reactor interior via lateral openings in the mixer stem or via the gas-injection unit between the two mixing elements. This has the advantage that the gas supplied is supplied by the flow as a result of the mixing movement.

According to a further preferred embodiment of the invention, the gas-injection unit has a porous structure for filtering gases. In this case, the gas-injection unit may be designed as a membrane with a microporous structure or else as a plastic frit.

According to a further preferred embodiment of the invention, a second duct via which media can be supplied or removed is provided in the mixer stem.

By a second duct being arranged in the mixer stem, a passage through the container wall, the arrangement of the mixer stem and the arrangement of two ducts through the container wall are produced. Just one aperture is therefore required in the container wall instead of three apertures.

According to a further preferred embodiment of the invention, the stem is designed as a tube, the free lumen of which forms the first duct. A second tube or a hose which forms the second duct can then be arranged in the free lumen of the stem. In this case, the hose or the tube is passed through the gas-injection unit and is sealed in relation thereto. This permits a relatively simple and cost-effective construction of the mixer stem and of its ducts.

The mixer may be sterilized by irradiation before or after penetrating the bioreactor.

The openings (Venturi nozzles) in the mixer plates may be tapered upward or downward, with a combination also being possible.

Further details of the invention emerge from the detailed description below and the attached drawings in which preferred embodiments of the invention are illustrated by way of example.

Figure 2:
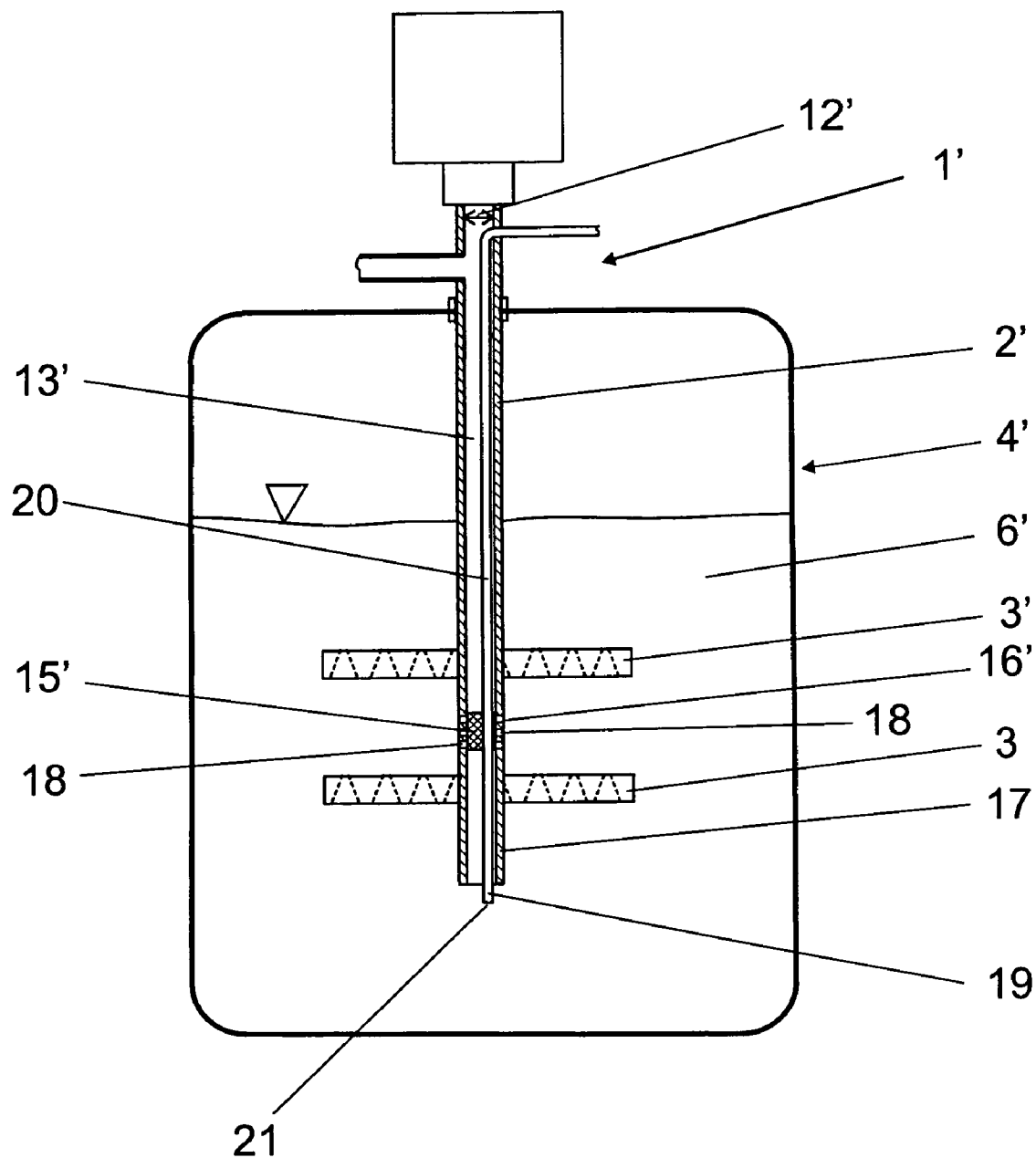

In the drawings:

FIG. 1 shows a side view of a vibration mixer arranged in a bioreactor having a flexible wall, and FIG. 2 shows a side view of a further vibration mixer arranged in a bioreactor.

A vibration mixer 1 essentially comprises a mixer stem 2 and a mixing element 3.

The vibration mixer 1 is used in a bioreactor 4 which is designed, for example, as a disposable bioreactor having a flexible wall 5 which surrounds a reactor interior 6. In this case, the mixer stem 2 penetrates a cover part 7 of the bioreactor 4, which cover part is arranged at the top in the vertical direction. The mixer stem 2 is sealed in relation to the cover part 7. The vibration mixer 1 is driven via a drive 8 which can be connected to the mixer stem 2 outside the reactor interior 6. The mixer stem 2 is thrown by the drive 8 into longitudinal movements which are transmitted to the mixing element 3 arranged on the mixer stem 2. In this case, the mixing element 3 is designed as a flat mixer plate 9 which has conically tapering holes 10 in the form of a type of Venturi nozzle.

The mixer stem 2 is designed as a tube 11, the free lumen 12 of which forms a duct 13. Outside the reactor interior 6, the mixer stem 2 has a lateral inlet 14 which produces a connection to the duct 13. According to the exemplary embodiment of FIG. 1, a gas-injection unit 15 is arranged just below the mixing element 3 at the free end of the mixer stem 2, which end is located at the bottom in the vertical direction, said gas-injection unit 15 being mounted upstream of an outlet 16 of the duct 13, which outlet is directed toward the reactor interior 6. The gas-injection unit 15 has a porous structure which is suitable for filtering gas supplied via the lateral inlet 14. The porous structure preferably has a pore size of less than 0.6 µm, preferably of less than 0.45 µm. In a preferred embodiment of the invention, the porous structure has hydrophobic properties. As a result, liquid is prevented from penetrating into the stem 13 when the pressure in the interior of the stem is lower than in reactor interior 6. Without the gas-injection unit 15, a liquid medium can also be supplied via the lateral inlet 14.

According to the exemplary embodiment of FIG. 2, the vibration mixer 1' has, on its mixer stem 2', two mixing elements 3, 3' which are arranged at a distance from each other. The gas-injection unit 15' is arranged between the two mixing elements 3, 3' in the duct 13'. In the region of the gas-injection unit 15', openings 18 via which gas filtered by the gas-injection unit 15' is discharged into the reactor interior 6' are arranged in the stem wall 17. The openings 18 therefore form an outlet 16'. A hose 19, the free lumen of which forms a second duct 20, is arranged in the free lumen 12' of the duct 13'. The hose 19 is guided laterally out of the mixer stem 2' in its upper region which is arranged outside the reactor interior 6' and is sealed in a gastight manner in relation to the stem wall 17. In the region of the gas-injection unit 15', the hose 19 is guided in a gastight manner through the latter. The second duct 20 likewise opens via its outlet 21 into the reactor interior 6'.

Both the mixer stem 2, 2' and the mixing element 3 or the mixing elements 3, 3' are formed from plastic and are connected to one another by welding or bonding. The hose 19 and the lateral inlet 14 are also formed from plastic. The vibration mixer 1, 1' can be sterilized by irradiation before or after penetrating the reactor interior 6, 6'.

The vibration mixer 1, 1' can be used as a disposable mixer.

The invention claimed is:

1. A vibration mixer (1) for use in disposable bioreactors (4, 4') having a flexible wall, the vibration mixer comprising: a mixer stem (2, 2') which can be thrown into longitudinal movements by a drive (8), at least one mixing element (3, 3') mounted on the mixer stem (2, 2'), the mixer stem (2, 2') being a tube with a free lumen (12, 12') defining at least one first duct (13, 13') having an inlet (14) external of the bioreactor (4, 4') for delivering gas into the free lumen (12, 12') and an outlet (16) toward a reactor interior (6, 6') for delivering the gas into the bioreactor (4, 4'), and a tubular member or a hose (19) arranged in the free lumen (12, 12') of the mixer stem (2, 2') to define a second duct (20) in the mixer stem (2, 2'), the second duct (20) having an inlet external of the bioreactor (4, 4') separated in a gas tight manner from the inlet (14) to the free lumen (12, 12') of the first duct (13, 13') and an outlet (21) in the bioreactor separated from the outlet (16) of the free lumen (12, 12') of the first duct (13, 13'), the second duct (20) supplying media to the bioreactor (4, 4') or removing media from the bioreactor (4, 4').

2. The vibration mixer as claimed in claim 1, characterized in that gas can be supplied via the at least one duct (13, 13'), and in that a gas-injection unit (15, 15') is mounted upstream of the outlet (16).

3. The vibration mixer as claimed in claim 2, characterized in that the gas-injection unit (15) forms the outlet.

4. The vibration mixer as claimed in claim 2, characterized in that the outlet (16) is arranged at a free end of the mixer stem that faces away from the drive.

5. The vibration mixer as claimed in claim 2, characterized in that the at least one mixing element (3, 3') comprises first and second mixing elements (3, 3'), the gas-injection unit (15') being mounted upstream of the first mixing element (3') toward the drive.

6. The vibration mixer as claimed in claim 2, characterized in that the gas-injection unit (15') is arranged on the mixer stem (2') between two mixing elements (3').

7. The vibration mixer as claimed in claims 2, characterized in that the gas-injection unit (15, 15') has a porous structure for filtering gases.

8. The vibration mixer as claimed in claims 2, characterized in that the gas-injection unit (15, 15') is designed as a membrane.

9. The vibration mixer as claimed in claims 2, characterized in that the gas-injection unit (15, 15') is designed as a plastic frit.

10. A vibration mixer for use in a disposable bioreactor (4') having a flexible wall, the vibration mixer comprising: a drive (8) disposed externally of the bioreactor (4'); a mixer stem (2') having a first end connected to the drive (8), a second end in the bioreactor (4') and a tubular outer wall extending substantially from the first end to the second end of the mixer stem (2'), at least one mixing element (3') mounted on a portion of the tubular outer wall of the mixer stem (2') in the bioreactor (4') and an inner wall (19) disposed within the mixer stem (2') to define a first duct (13') and a second duct (20) in the mixer stem (2'), the first and second ducts (13', 20) having inlets (14) external of the bioreactor (4') that are separated from one another in a gas tight manner and outlets (16, 21) in the bioreactor (4') separated from one another, whereby the first duct (13') accommodates a supply of gas to the bioreactor (4') and the second duct (20) enables media to be supplied to or removed from the bioreactor (4').

11. The vibration mixer as claimed in claim 10, wherein the outlet (16') of the first duct (13') is spaced from the outlet (21) of the second duct (20).

12. The vibration mixer as claimed in claim 11, wherein the outlet (16') of the first duct (13') is between the mixing element (3') and the second end of the mixer stem (2').

13. The vibration mixer as claimed in claim 11, wherein the at least one mixing element (3') comprises two mixing elements (3') spaced apart along the mixer stem (2').

14. The vibration mixer as claimed in claim 13, wherein the outlet (16') of the first duct (13') is between the mixing elements (3').

15. The vibration mixer as claimed in claim 11, wherein the mixing element (3') is between the outlet (21) of the second duct (20) and the first end of the mixer stem (2').

16. The vibration mixer as claimed in claim 10, wherein the inner wall (19) is defined by a tube or a hose extending at least partly through the mixer stem (2').

* * * * *